United States Patent [19]
Setlak et al.

[11] Patent Number: 6,088,471
[45] Date of Patent: *Jul. 11, 2000

[54] FINGERPRINT SENSOR INCLUDING AN ANISOTROPIC DIELECTRIC COATING AND ASSOCIATED METHODS

[75] Inventors: Dale R. Setlak; Nicolass W. Van Vonno, both of Melbourne; Mike Newton, Palm Bay; Matthew M. Salatino, Satellite Beach, all of Fla.

[73] Assignee: Authentec, Inc., Melbourne, Fla.

[*] Notice: This patent is subject to a terminal disclaimer.

[21] Appl. No.: 08/858,005

[22] Filed: May 16, 1997

[51] Int. Cl.$^7$ ........................................................ G06K 9/00
[52] U.S. Cl. ............................................ 382/124; 382/116
[58] Field of Search ..................................... 382/115, 116, 382/124, 125, 126; 340/825.3; 283/67, 68, 69; 430/286.1

[56] References Cited

U.S. PATENT DOCUMENTS

| | | |
|---|---|---|
| 3,781,855 | 12/1973 | Killen . |
| 4,202,120 | 5/1980 | Engel . |
| 4,210,899 | 7/1980 | Swonger et al. . |
| 4,353,056 | 10/1982 | Tsikos . |
| 4,418,472 | 12/1983 | Lorenze, Jr. . |
| 4,557,504 | 12/1985 | Kuhns . |
| 4,634,228 | 1/1987 | Iwasaki et al. . |
| 4,675,224 | 6/1987 | Hosokawa . |
| 4,737,398 | 4/1988 | Ikenaga et al. . |
| 4,768,021 | 8/1988 | Ferraro . |
| 4,798,765 | 1/1989 | Ishizaka et al. . |
| 4,811,414 | 3/1989 | Fishbine et al. . |
| 4,910,068 | 3/1990 | Takagi et al. . |
| 4,923,763 | 5/1990 | Nakamura et al. . |
| 4,983,846 | 1/1991 | Rios et al. . |
| 4,993,068 | 2/1991 | Piosenka et al. . |
| 5,139,849 | 8/1992 | Takagi et al. . |
| 5,222,152 | 6/1993 | Fishbine et al. . |
| 5,224,173 | 6/1993 | Kuhns et al. . |
| 5,245,329 | 9/1993 | Gokcebay . |
| 5,280,527 | 1/1994 | Gullman et al. . |
| 5,325,442 | 6/1994 | Knapp . |
| 5,363,453 | 11/1994 | Gagne et al. . |
| 5,386,104 | 1/1995 | Sime . |
| 5,467,403 | 11/1995 | Fishbine et al. . |
| 5,509,083 | 4/1996 | Abtahi et al. . |
| 5,513,272 | 4/1996 | Bogosian, Jr. . |
| 5,541,994 | 7/1996 | Tomko et al. . |
| 5,546,471 | 8/1996 | Merjanian . |
| 5,583,474 | 12/1996 | Mizoguchi et al. . |
| 5,598,474 | 1/1997 | Johnson . |
| 5,603,179 | 2/1997 | Adams . |
| 5,613,712 | 3/1997 | Jeffers . |
| 5,623,552 | 4/1997 | Lane . |
| 5,723,262 | 3/1998 | Nakamura et al. .................. 430/286.1 |

OTHER PUBLICATIONS

M. Tartagni et al., "A 390 dpi live fingerprint imager based on feedback capacitive sensing scheme", 1997 IEEE International Solid–State Circuits Conference, Digest of Technical Papers, ISSCC, San Francisco, CA, Feb. 1997, pp. 200–201, 456, XP002077718, ISBN 0–7803–3721–2, 1997, New York.

*Primary Examiner*—Amelia Au
*Assistant Examiner*—Vikkram Bali
*Attorney, Agent, or Firm*—Allem,. Dyer, Doppelt, Milbrath & Gilchrist, P.A.

[57] ABSTRACT

A fingerprint sensor includes an integrated circuit die and a protective covering of a z-axis anisotropic dielectric material. The die includes a conductive layer defining an array of electric field sensing electrodes. The z-axis anisotropic dielectric layer focusses an electric field at each of the electric field sensing electrodes. In other words, the dielectric covering may be relatively thick, but not result in defocussing of the electric fields propagating through the dielectric covering because of the z-axis anisotropy of the material. The z-axis anisotropic dielectric layer may be provided by a plurality of oriented dielectric particles in a cured matrix. For example, the z-axis anisotropic dielectric layer may comprise barium titanate in a polyimide matrix. The conductive layer preferably comprises a plurality of capacitive coupling pads for permitting capacitive coupling with the integrated circuit die. Accordingly, the dielectric covering is preferably continuous over the capacitive coupling pads and the array of electric field sensing electrodes. The z-axis dielectric layer also advantageously reduces cross-talk between adjacent capacitive coupling pads.

58 Claims, 6 Drawing Sheets

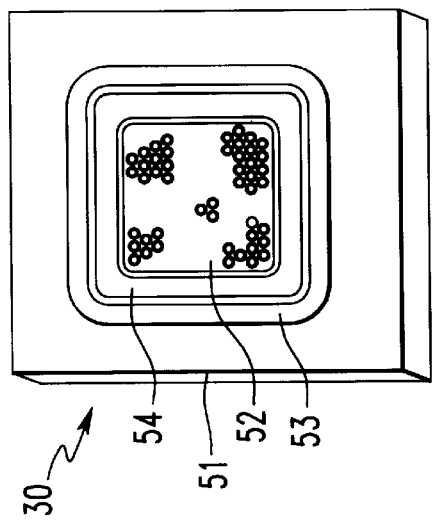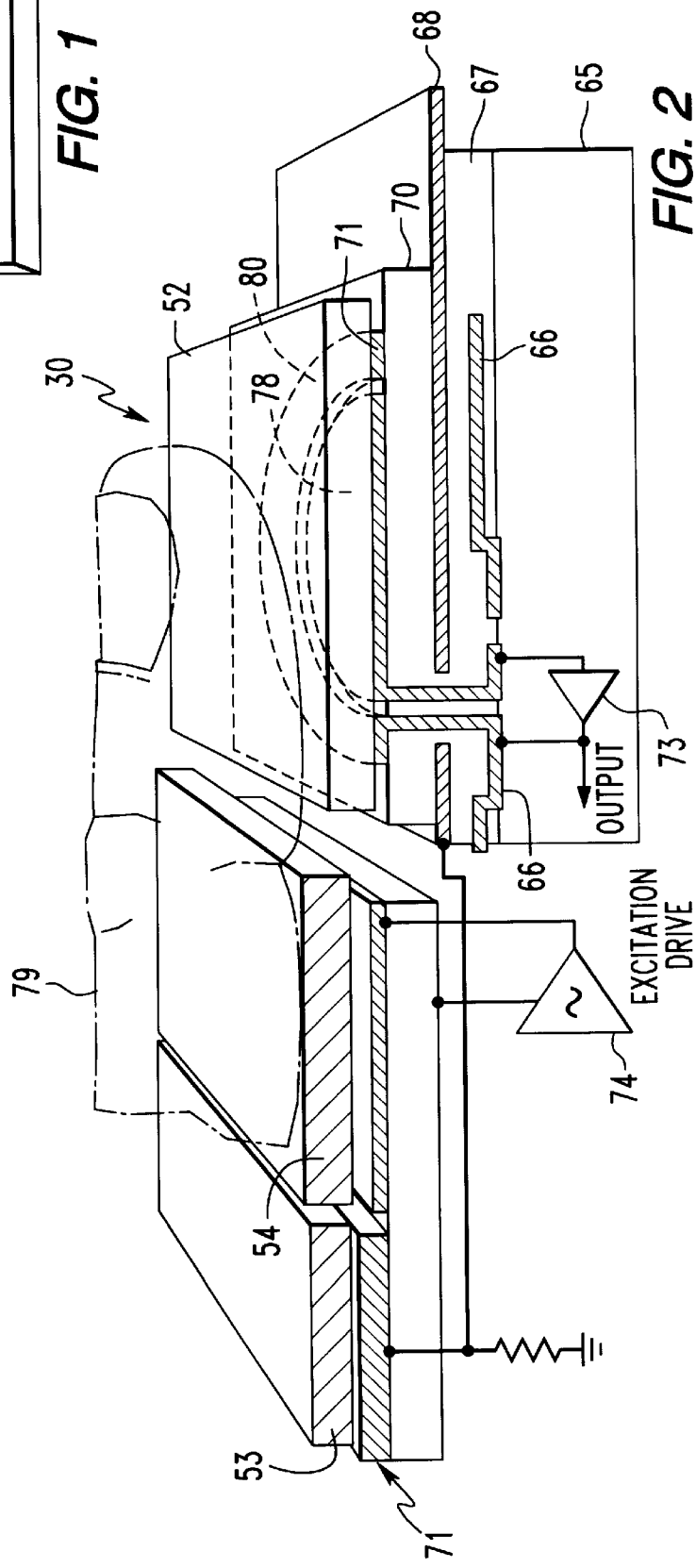

FINGERPRINT SENSOR INCLUDING AN ANISOTROPIC DIELECTRIC COATING AND ASSOCIATED METHODS

FIELD OF THE INVENTION

The present invention relates to the field of personal identification and verification, and, more particularly, to the field of fingerprint sensing and processing.

BACKGROUND OF THE INVENTION

Fingerprint sensing and matching is a reliable and widely used technique for personal identification or verification. In particular, a common approach to fingerprint identification involves scanning a sample fingerprint or an image thereof and storing the image and/or unique characteristics of the fingerprint image. The characteristics of a sample fingerprint may be compared to information for reference fingerprints already in a database to determine proper identification of a person, such as for verification purposes.

A typical electronic fingerprint sensor is based upon illuminating the finger surface using visible light, infrared light, or ultrasonic radiation. The reflected energy is captured with some form of camera, for example, and the resulting image is framed, digitized and stored as a static digital image. For example, U.S. Pat. No. 4,210,899 to Swonger et al. discloses an optical scanning fingerprint reader cooperating with a central processing station for a secure access application, such as admitting a person to a location or providing access to a computer terminal. U.S. Pat. No. 4,525,859 to Bowles similarly discloses a video camera for capturing a fingerprint image and uses the minutiae of the fingerprints, that is, the branches and endings of the fingerprint ridges, to determine a match with a database of reference fingerprints.

Unfortunately, optical sensing may be affected by stained fingers or an optical sensor may be deceived by presentation of a photograph or printed image of a fingerprint rather an a true live fingerprint. In addition, optical schemes may require relatively large spacings between the finger contact surface and associated imaging components. Moreover, such sensors typically require precise alignment and complex scanning of optical beams. Accordingly, optical sensors may thus be bulky and be susceptible to shock, vibration and surface contamination. Accordingly, an optical fingerprint sensor may be unreliable in service in addition to being bulky and relatively expensive due to optics and moving parts.

U.S. Pat. No. 4,353,056 to Tsikos discloses another approach to sensing a live fingerprint. In particular, the patent discloses an array of extremely small capacitors located in a plane parallel to the sensing surface of the device. When a finger touches the sensing surface and deforms the surface, a voltage distribution in a series connection of the capacitors may change. The voltages on each of the capacitors is determined by multiplexor techniques. Unfortunately, the resilient materials required for the sensor may suffer from long term reliability problems. In addition, multiplexing techniques for driving and scanning each of the individual capacitors may be relatively slow and cumbersome. Moreover, noise and stray capacitances may adversely affect the plurality of relatively small and closely spaced capacitors.

U.S. Pat. No. 5,325,442 to Knapp discloses a fingerprint sensor including a plurality of sensing electrodes. Active addressing of the sensing electrodes is made possible by the provision of a switching device associated with each sensing electrode. A capacitor is effectively formed by each sensing electrode in combination with the respective overlying portion of the finger surface which, in turn, is at ground potential. The sensor may be fabricated using semiconductor wafer and integrated circuit technology. The dielectric material upon which the finger is placed may be provided by silicon nitride or a polyimide which may be provided as a continuous layer over an array of sensing electrodes. Further conductors may be provided on the surface of the dielectric material remote from the sensing electrodes and extending over regions between the sensing electrodes, for example, as lines or in grid form, which conductors are grounded in order to improve the electrical contact to the finger surface.

Unfortunately, driving the array of closely spaced sensing electrodes as disclosed in the Knapp et al. patent may be difficult since adjacent electrodes may affect one another. Another difficulty with such a sensor may be its ability to distinguish ridges and valleys of a fingerprint when the conductivity of the skin and any contaminants may vary widely from person-to-person and even over a single fingerprint. Yet another difficulty with such a sensor, as with many optical sensors, is that different portions of the fingerprint may require relatively complicated post image collection processing to provide for usable signal levels and contrast to thereby permit accurate determination of the ridges and valleys of the fingerprint. For example, U.S. Pat. No. 4,811,414 to Fishbine et al. discloses methods for noise averaging, illumination equalizing, directional filtering, curvature correcting, and scale correcting for an optically generated fingerprint image. Unfortunately, the various processing steps are complex and require considerable computational power in a downstream processor. Signal processing of other fingerprint circuits may also be relatively complicated and therefore expensive and/or slow.

Greater advances in fingerprint sensing and matching for identification and verification are desirable for many applications. Unfortunately, current sensor and their associated circuitry may be too bulky, expensive and unreliable for a great many applications which would otherwise benefit from fingerprint identification and verification technology. Moreover, integrated circuit technology is not typically comfortable with having an exposed die. In addition, moisture and other contaminants may quickly damage an integrated circuit.

SUMMARY OF THE INVENTION

In view of the foregoing background, it is therefore an object of the present invention to provide a fingerprint sensor and a method of making the sensor so that the sensor has a sufficient protective outer covering, but also readily generates an accurate image of the fingerprint through the protective covering.

It is another object of the present invention to provide such a protective covering and yet permit signals and power to be exchanged with the integrated circuit die of the sensor.

These and other objects, features and advantages in accordance with the present invention are provided by a fingerprint sensor comprising an integrated circuit die including a conductive layer defining an array of electric field sensing electrodes, and a dielectric covering adjacent the array of electric field sensing electrodes, and wherein the dielectric covering comprises a z-axis anisotropic dielectric layer for focussing an electric field at each of the electric field sensing electrodes. In other words, the dielectric covering may be relatively thick, but not result in defocussing of the electric fields propagating through the dielectric covering because of the z-axis anisotropy of the material.

For example, the z-axis anisotropic dielectric layer may have a thickness in range of about 0.0001 to 0.004 inches thick. Of course, the z-axis anisotropic dielectric layer is also preferably chemically resistant and mechanically strong to withstand contact with fingers, and to permit periodic cleanings with solvents.

The z-axis anisotropic dielectric layer may preferably define an outermost protective surface for the integrated circuit die. Accordingly, the dielectric covering may further include at least one relatively thin layer of an oxide, nitride, carbide, or diamond on the integrated circuit die and beneath the z-axis anisotropic dielectric layer.

The z-axis anisotropic dielectric layer may be provided by a plurality of oriented dielectric particles in a cured matrix. For example, the z-axis anisotropic dielectric layer may comprise barium titanate in a polyimide matrix. The z-axis dielectric layer may also be provided by a plurality of high dielectric portions aligned with corresponding electric field sensing electrodes, and a surrounding matrix of lower dielectric portions.

Another aspect of the invention relates to being able to completely cover the entire upper surface of the integrated circuit die, and permit electrical connection to the external devices and circuits. The conductive layer preferably comprises a plurality of capacitive coupling pads for permitting capacitive coupling with the integrated circuit die. Accordingly, the dielectric covering is preferably continuous over the capacitive coupling pads and the array of electric field sensing electrodes. The z-axis dielectric layer also advantageously reduces cross-talk between adjacent capacitive coupling pads. This embodiment of the invention presents no penetrations through the dielectric covering for moisture to enter and damage the integrated circuit die.

The fingerprint sensor preferably includes a package surrounding the integrated circuit die and dielectric covering. For the fingerprint sensor, the package preferably has an opening aligned with the array of electric field sensing electrodes. One or more finger contacting electrodes may be carried by the package and electrically connected to the integrated circuit die.

A method aspect of the invention is for making a fingerprint sensor. The method preferably comprises the steps of: forming an integrated circuit die comprising at least one conductive layer defining an array of electric field sensing electrodes for sensing a fingerprint; and forming a dielectric covering adjacent the array of electric field sensing electrodes of the integrated circuit die and for contact by a finger, the dielectric covering comprising a z-axis anisotropic dielectric layer for focussing an electric field at each of the electric field sensing electrodes. In embodiments of the invention other than for a fingerprint sensor, the z-axis anisotropic layer may provide and effective way to further protect the integrated circuit die while permitting capacitive coupling of signals and power to the circuits of the die.

BRIEF DESCRIPTION OF THE DRAWINGS

FIG. 1 is a top plan view of a fingerprint sensor in accordance with the present invention.

FIG. 2 is a schematic view of a circuit portion of the fingerprint sensor as shown in FIG. 1.

DETAILED DESCRIPTION OF THE PREFERRED EMBODIMENTS

Figure 3:
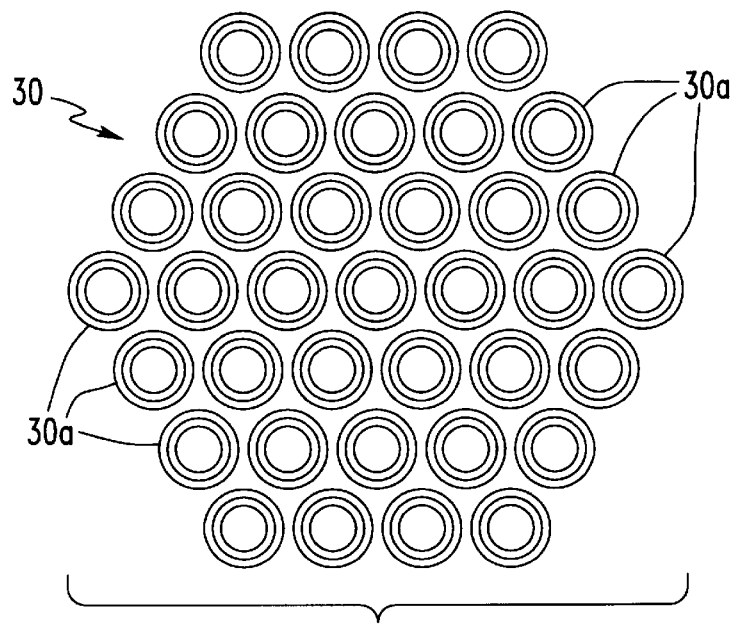
FIG. 3 is a greatly enlarged top plan view of the sensing portion of the fingerprint sensor as shown in FIG. 1.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. The scaling of various features, particularly layers in the drawing figures, have been exaggerated for clarity of explanation.

Referring to FIGS. 1–3, the fingerprint sensor 30 in accordance with the invention is initially described. The illustrated sensor 30 includes a housing or package 51, a dielectric layer 52 exposed on an upper surface of the package which provides a placement surface for the finger, and a plurality of output pins, now shown. A first conductive strip or external electrode 54 around the periphery of the dielectric layer 52, and a second external electrode 53 provide contact electrodes for the finger 79 as described in greater detail below. The sensor 30 may provide output signals in a range of sophistication levels depending on the level of processing incorporated in the package as would be readily understood by those skilled in the art.

The sensor 30 includes a plurality of individual pixels or sensing elements 30a arranged in array pattern as perhaps best shown in FIG. 3. As would be readily understood by those skilled in the art, these sensing elements are relatively small so as to be capable of sensing the ridges 59 and intervening valleys 60 of a typical fingerprint. As will also be readily appreciated by those skilled in the art, live fingerprint readings as from the electric field sensor 30 in accordance with the present invention may be more reliable than optical sensing, because the impedance of the skin of a finger in a pattern of ridges and valleys is extremely difficult to simulate. In contrast, an optical sensor may be deceived by a readily deceived by a photograph or other similar image of a fingerprint, for example.

The sensor 30 includes a substrate 65, and one or more active semiconductor devices formed thereon, such as the schematically illustrated amplifier 73. A first metal layer 66 interconnects the active semiconductor devices. A second or ground plane electrode layer 68 is above the first metal layer 66 and separated therefrom by an insulating layer 67. A third metal layer 71 is positioned over another dielectric layer 70. In the illustrated embodiment, the first external electrode 54 is connected to an excitation drive amplifier 74 which, in turn, drives the finger 79 with a signal may be typically in the range of about 1 KHz to 1 MHz. Accordingly, the drive or excitation electronics are thus relatively uncomplicated and the overall cost of the sensor 30 may be relatively low, while the reliability is great.

An illustratively circularly shaped electric field sensing electrode 78 is on the insulating layer 70. The sensing electrode 78 may be connected to sensing integrated electronics, such as the illustrated amplifier 73 formed adjacent the substrate 65 as schematically illustrated, and as would be readily appreciated by those skilled in the art.

An annularly shaped shield electrode 80 surrounds the sensing electrode 78 in spaced relation therefrom. As would be readily appreciated by those skilled in the art, the sensing electrode 78 and its surrounding shield electrode 80 may have other shapes, such as hexagonal, for example, to facilitate a close packed arrangement or array of pixels or sensing elements 30*a*. The shield electrode 80 is an active shield which is driven by a portion of the output of the amplifier 73 to help focus the electric field energy and, moreover, to thereby reduce the need to drive adjacent electric field sensing electrodes 78.

The sensor 30 includes only three metal or electrically conductive layers 66, 68 and 71. The sensor 30 can be made without requiring additional metal layers which would otherwise increase the manufacturing cost, and, perhaps, reduce yields. Accordingly, the sensor 30 is less expensive and may be more rugged and reliable than a sensor including four or more metal layers as would be appreciated by those skilled in the art.

Another important aspect of the present invention is that the amplifier 73 may be operated at a gain of greater than about one to drive the shield electrode 80. Stability problems do not adversely affect the operation of the amplifier 73. Moreover, the common mode and general noise rejection are greatly enhanced according to this feature of the invention. In addition, the gain greater than one tends to focus the electric field with resect to the sensing electrode 78 as will be readily appreciated by those skilled in the art.

In general, the sensing elements 30*a* operate at very low currents and at very high impedances. For example, the output signal from each sensing electrode 78 is desirably about 5 to 10 millivolts to reduce the effects of noise and permit further processing of the signals. The approximate diameter of each sensing element 30*a*, as defined by the outer dimensions of the shield electrode 80, may be about 0.002 to 0.005 inches in diameter. The ground plane electrode 68 protects the active electronic devices from unwanted excitation. The various signal feedthrough conductors for the electrodes 78, 80 to the active electronic circuitry may be readily formed as would be understood by those skilled in the art.

The overall contact or sensing surface for the sensor 30 may desirably be about 0.5 by 0.5 inches—a size which may be readily manufactured and still provide a sufficiently large surface for accurate fingerprint sensing and identification. The sensor 30 in accordance with the invention is also fairly tolerant of dead pixels or sensing elements 30*a*. A typical sensor 30 includes an array of about 256 by 256 pixels or sensor elements, although other array sizes are also contemplated by the present invention. The sensor 30 may also be fabricated at one time using primarily conventional semiconductor manufacturing techniques to thereby significantly reduce the manufacturing costs.

Figure 4:
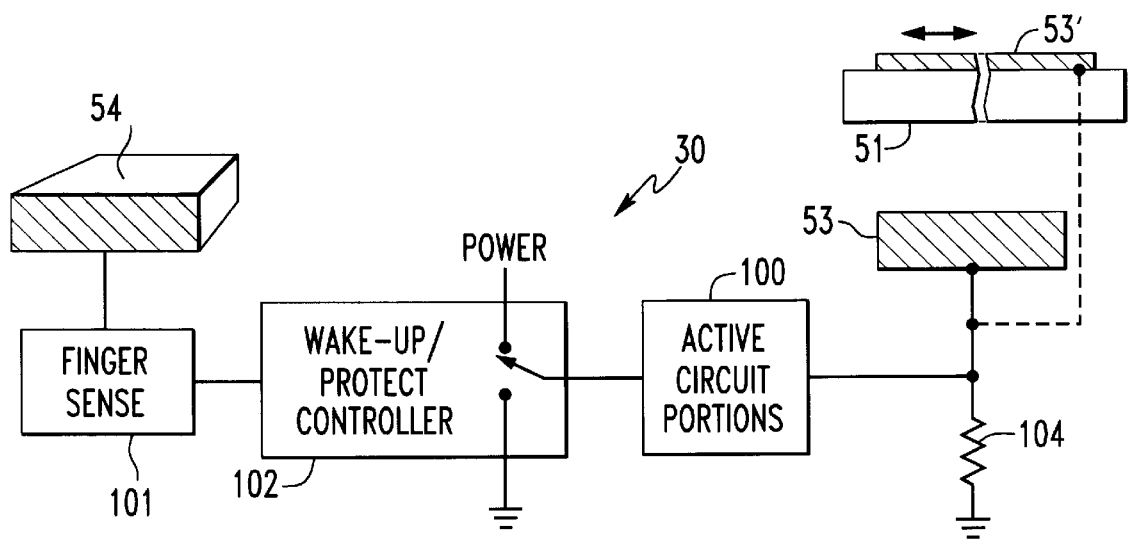
FIG. 4 is a schematic diagram of another circuit portion of the fingerprint sensor as shown in FIG. 1.

Turning now additionally to FIG. 4, another aspect of the sensor 30 of the invention is described. The sensor may include power control means for controlling operation of active circuit portions 100 based upon sensing finger contact with the first external electrode 54 as determined by the illustrated finger sense block or circuit 101. For example, the finger sense circuit 101 may operate based upon a change in impedance to an oscillator to thereby determine finger contact. Of course, other approaches for sensing contact with the finger are also contemplated by the invention. The power control means may include wake-up means for only powering active circuit portions upon sensing finger contact with the first external electrode to thereby conserve power. Alternately or additionally, the power control means may further comprise protection means for grounding active circuit portions upon not sensing finger contact with the first external electrode. In the illustrated embodiment, a combination of wake-up and protection controller circuits 101 are illustrated.

Moreover, the fingerprint sensor 30 may further comprise finger charge bleed means for bleeding a charge from a finger or other object upon contact therewith. The finger charge bleed means may be provided by the second external electrode 53 carried by the package 51 for contact by a finger, and a charge bleed resistor 104 connected between the second external electrode and an earth ground. As schematically illustrated in the upper right hand portion of FIG. 4, the second electrode may alternately be provided by a movable electrically conductive cover 53' slidably connected to the package 51 for covering the opening to the exposed upper dielectric layer 52. A pivotally connected cover is also contemplated by the present invention. Accordingly, under normal conditions, the charge would be bled from the finger as the cover 53' is moved to expose the sensing portion of the sensor 30.

In addition, the finger charge bleed means and power control means may be such that the active portions remain grounded until the charge bleed means can remove the charge on the finger before powering the active circuit portions, such as by providing a brief delay during wake-up sufficient to permit the charge to be discharged through the resistor 104 as would be readily understood by those skilled in the art. Accordingly, power may be conserved in the sensor 30 and ESD protection provided by the sensor so that the sensor is relatively inexpensive, yet robust and conserves power.

Figure 5:
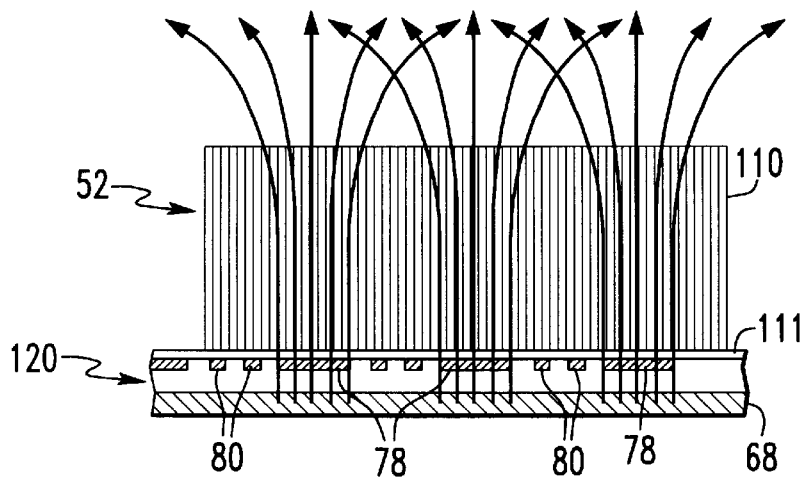
FIG. 5 is a greatly enlarged side cross-sectional view of a portion of the fingerprint sensor as shown in FIG. 1.

Referring now additionally to FIG. 5 yet another significant feature of the sensor 30 is described. The dielectric covering 52 may preferably comprise a z-axis anisotropic dielectric layer 110 for focussing an electric field, shown by the illustrated field lines, at each of the electric field sensing electrodes 78. In other words, the dielectric layer 110 may be relatively thick, but not result in defocussing of the electric fields propagating therethrough because of the z-axis anisotropy of the material. Typically there would be a trade-off between field focus and mechanical protection. Unfortunately, a thin film which is desirable for focussing, may permit the underlying circuit to be more easily subject to damage.

The z-axis anisotropic dielectric layer 110 of the present invention, for example, may have a thickness in the range of about 0.0001 to 0.004 inches. Of course, the z-axis anisotropic dielectric layer 110 is also preferably chemically resistant and mechanically strong to withstand contact with fingers, and to permit periodic cleanings with solvents. The z-axis anisotropic dielectric layer 110 may preferably define an outermost protective surface for the integrated circuit die 120. Accordingly, the overall dielectric covering 52 may further include at least one relatively thin oxide, nitride, carbide, or diamond layer 111 on the integrated circuit die 120 and beneath the z-axis anisotropic dielectric layer 110. The thin layer 111 will typically be relatively hard, and the z-axis anisotropic dielectric layer 110 is desirably softer to thereby absorb more mechanical activity.

The z-axis anisotropic dielectric layer 110 may be provided by a plurality of oriented dielectric particles in a cured matrix. For example, the z-axis anisotropic dielectric layer 110 may comprise barium titanate in a polyimide matrix. Those of skill in the art will appreciate other materials exhibiting z-axis anisotropy suitable for the present invention. For example, certain ceramics exhibit dielectric anisotropy as would also be appreciated by those skilled in the art.

Figure 6:
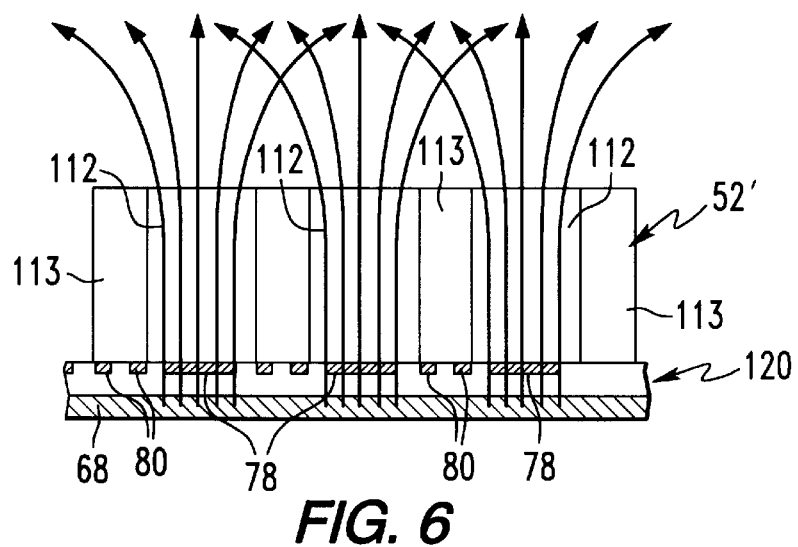
FIG. 6 is a greatly enlarged side cross-sectional view of a portion of an alternate embodiment of the fingerprint sensor in accordance with the invention.

Turning to FIG. 6, another variation of a z-axis dielectric covering 52' is schematically shown by a plurality of high dielectric portions 112 aligned with corresponding electric field sensing electrodes 78, and a surrounding matrix of lower dielectric portions 113. This embodiment of the dielectric covering 52' may be formed in a number of ways, such as by forming a layer of either the high dielectric or low dielectric portions, selectively etching same, and filling the openings with the opposite material. Another approach may be to use polarizable microcapsules and subjecting same to an electric field during curing of a matrix material. A material may be compressed to cause the z-axis anisotropy. Laser and other selective processing techniques may also be used as would be readily understood by those skilled in the art.

Figure 7:
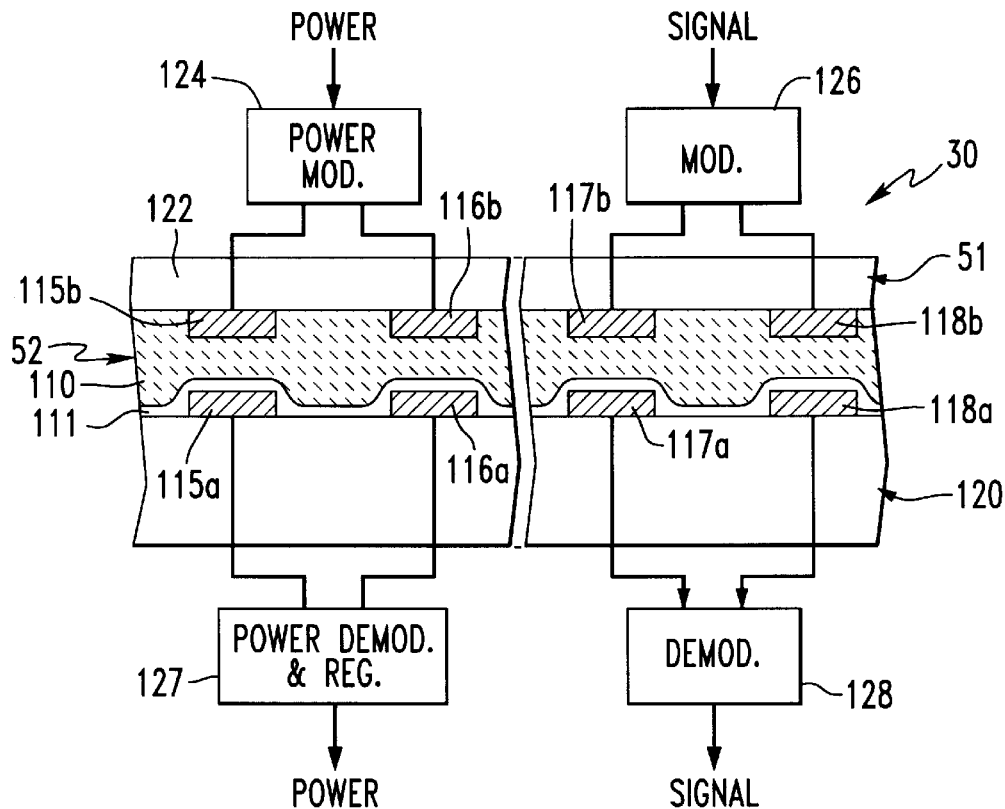
FIG. 7 is a greatly enlarged side cross-sectional view of another portion of the fingerprint sensor as shown in FIG. 1.

Another aspect of the invention relates to being able to completely cover and protect the entire upper surface of the integrated circuit die 120, and still permit connection and communication with the external devices and circuits as now further explained with reference to FIG. 7. The third metal layer 71 (FIG. 2) preferably further includes a plurality of capacitive coupling pads 116a–118a for permitting capacitive coupling of the integrated circuit die 120. Accordingly, the dielectric covering 52 is preferably continuous over the capacitive coupling pads 116a–118a and the array of electric field sensing electrodes 78 of the pixels 30a (FIG. 1). In sharp contrast to this feature of the present invention, it is conventional to create openings through an outer coating to electrically connect to the bond pads. Unfortunately, these openings would provide pathways for water and/or other contaminants to come in contact with and damage the die.

A portion of the package 51 includes a printed circuit board 122 which carries corresponding pads 115b–118b. A power modulation circuit 124 is coupled to pads 115b–116b, while a signal modulation circuit 126 is illustrative coupled to pads 117b–118b. As would be readily understood by those skilled in the art, both power and signals may be readily coupled between the printed circuit board 122 and the integrated circuit die 120, further using the illustrated power demodulation/regulator circuit 127, and the signal demodulation circuit 128. The z-axis anisotropic dielectric layer 110 also advantageously reduces cross-talk between adjacent capacitive coupling pads. This embodiment of the invention 30 presents no penetrations through the dielectric covering 52 for moisture to enter and damage the integrated circuit die 120. In addition, another level of insulation is provided between the integrated circuit and the external environment.

For the illustrated fingerprint sensor 30, the package 51 preferably has an opening aligned with the array of electric field sensing electrodes 78 (FIGS. 1–3). The capacitive coupling and z-axis anisotropic layer 110 may be advantageously used in a number of applications in addition to the illustrated fingerprint sensor 30, and particularly where it is desired to have a continuous film covering the upper surface of the integrated circuit die 120 and pads 116a–118a.

Further aspects of the manufacturing of the sensor 30 including the z-axis anisotropic dielectric material are explained in U.S. Pat. No. 5,887,343, issued Mar. 30, 1999, entitled "Direct Chip Attachment Method", assigned to the present assignee, and the entire disclosure of which is incorporated herein by reference.

Figure 8:
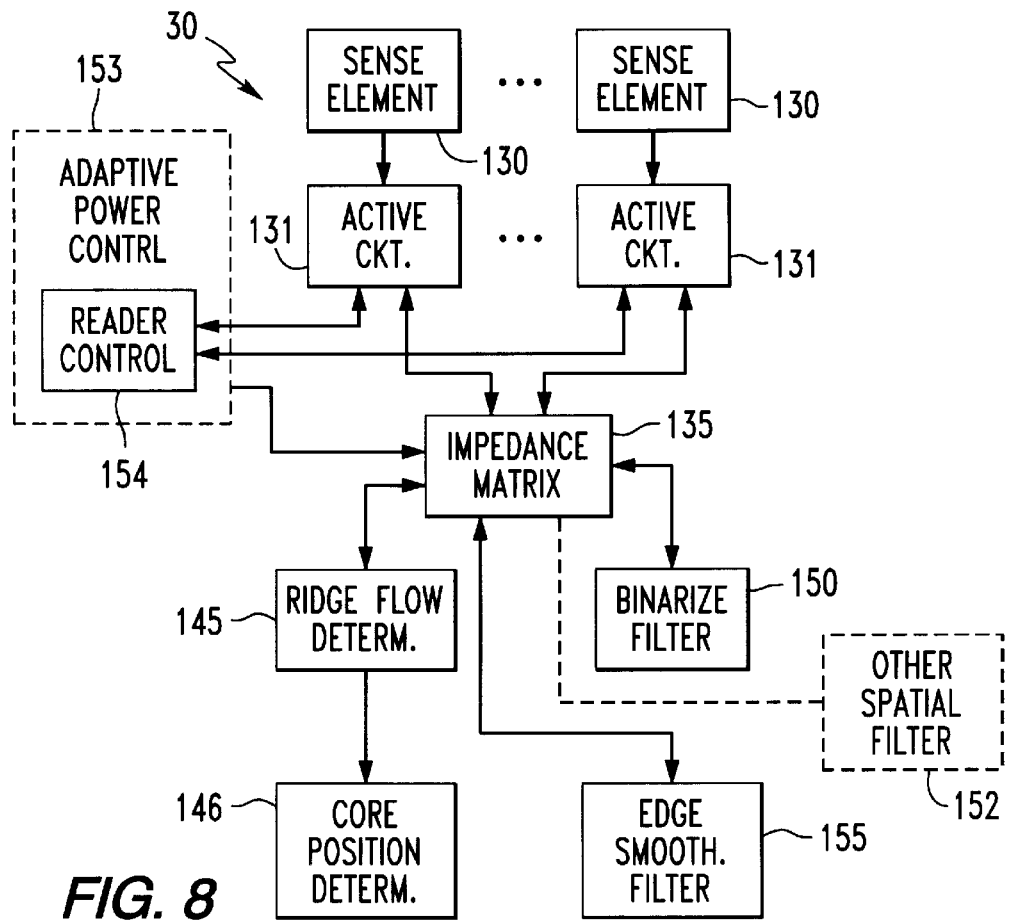
FIG. 8 is a schematic block diagram of yet another circuit portion of the fingerprint sensor as shown in FIG. 1.
Figure 9:
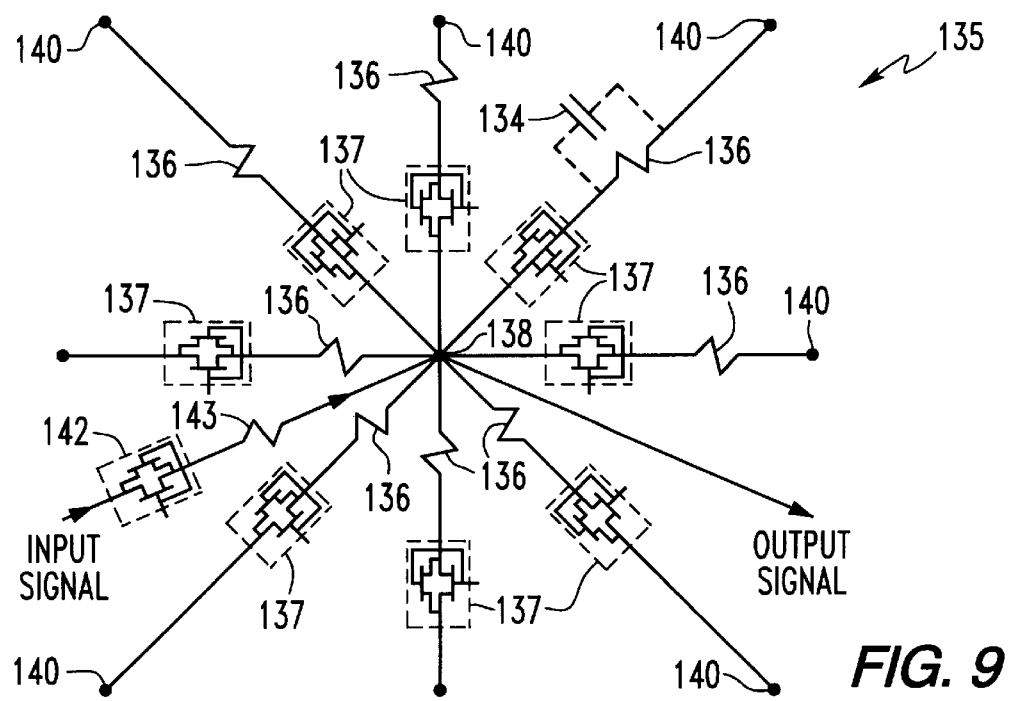
FIG. 9 is a schematic circuit diagram of a portion of the circuit as shown in FIG. 8.

Referring additionally to FIGS. 8 and 9, impedance matrix filtering aspects of the invention are now described. As shown in FIG. 8, the fingerprint sensor 30 may be considered as comprising an array of fingerprint sensing elements 130 and associated active circuits 131 for generating signals relating to the fingerprint image. The illustrated sensor 30 also includes an impedance matrix 135 connected to the active circuits for filtering the signals therefrom.

As shown with more particular reference to FIG. 9, the impedance matrix 135 includes a plurality of impedance elements 136 with a respective impedance element connectable between each active circuit of a respective fingerprint sensing element as indicated by the central node 138, and the other active circuits (outer nodes 140). The impedance matrix 135 also includes a plurality of switches 137 with a respective switch connected in series with each impedance element 136. An input signal may be supplied to the central node 138 via the illustrated switch 142 and its associated impedance element 143. The impedance element may one or more of a resistor as illustrated, and a capacitor 134 as would be readily appreciated by those skilled in the art.

Filter control means may operate the switches 137 to perform processing of the signals generated by the active circuits 131. In one embodiment, the fingerprint sensing elements 130 may be electric field sensing electrodes 78, and the active circuits 131 may be amplifiers 73 (FIG. 2). Of course other sensing elements and active circuits may also benefit from the impedance matrix filtering of the present invention as would be readily understood by those skilled in the art.

Ridge flow determining means 145 may be provided for selectively operating the switches 137 of the matrix 135 to determine ridge flow directions of the fingerprint image. More particularly, the ridge flow determining means 145 may selectively operate the switches 137 for determining signal strength vectors relating to ridge flow directions of the fingerprint image. As would be readily understood by those skilled in the art, the ridge flow directions may be determined based upon well known rotating slit principles.

The sensor 30 may include core location determining means 146 cooperating with the ridge flow determining means 145 for determining a core location of the fingerprint image. The position of the core is helpful, for example, in extracting and processing minutiae from the fingerprint image as would also be readily understood by those skilled in the art.

As also schematically illustrated in FIG. 8, a binarizing filter 150 may be provided for selectively operating the switches 137 to convert a gray scale fingerprint image to a binarized fingerprint image. Considered another way, the impedance matrix 135 may be used to provide dynamic image contrast enhancement. In addition, an edge smoothing filter 155 may be readily implemented to improve the image. As also schematically illustrated other spatial filters 152 may also be implemented using the impedance matrix 135 for selectively operating the switches 137 to spatially filter the fingerprint image as would be readily appreciated by those of skill in the art. Accordingly, processing of the fingerprint image may be carried out at the sensor 30 and thereby reduce additional downstream computational requirements.

As shown in the illustrated embodiment of FIG. 9, the impedance matrix 135 may comprise a plurality of impedance elements with a respective impedance element 136 connectable between each active circuit for a given fingerprint sensing element 130 and eight other active circuits for respective adjacent fingerprint sensing elements.

Yet another aspect of the invention is the provision of control means 153 for sequentially powering sets of active circuits 131 to thereby conserve power. Of course, the respective impedance elements 136 are desirably also sequentially connected to perform the filtering function. The powered active circuits 131 may be considered as defining a cloud or kernel as would be readily appreciated by those skilled in the art. The power control means 153 may be operated in an adaptive fashion whereby the size of the area used for filtering is dynamically changed for preferred image characteristics as would also be readily understood by those skilled in the art. In addition, the power control means 153 may also power only certain ones of the active circuits corresponding to a predetermined area of the array of sensing elements 130. For example, every other active circuit 131 could be powered to thereby provide a larger area, but reduced power consumption as would also be understood by those skilled in the art.

Reader control means 154 may be provided to read only predetermined subsets of each set of active circuits 131 so that a contribution from adjacent active circuits is used for filtering. In other words, only a subset of active circuits 131 are typically simultaneously read although adjacent active circuits 131 and associated impedance elements 136 are also powered and connected, respectively. For example, 16 impedance elements 136 could define a subset and be readily simultaneously read. The subset size could be optimized for different sized features to be determined as would be readily appreciated by those skilled in the art.

Accordingly, the array of sense elements 130 can be quickly read, and power consumption substantially reduced since all of the active circuits 131 need not be powered for reading a given set of active circuits. For a typical sensor, the combination of the power control and impedance matrix features described herein may permit power savings by a factor of about 10 as compared to powering the full array.

It is another important advantage of the fingerprint sensor 30 according to present invention to guard against spoofing or deception of the sensor into incorrectly treating a simulated image as a live fingerprint image. For example, optical sensors may be deceived or spoofed by using a paper with a fingerprint image thereon. The unique electric field sensing of the fingerprint sensor 30 of the present invention provides an effective approach to avoiding spoofing based upon the complex impedance of a finger.

Figure 10:
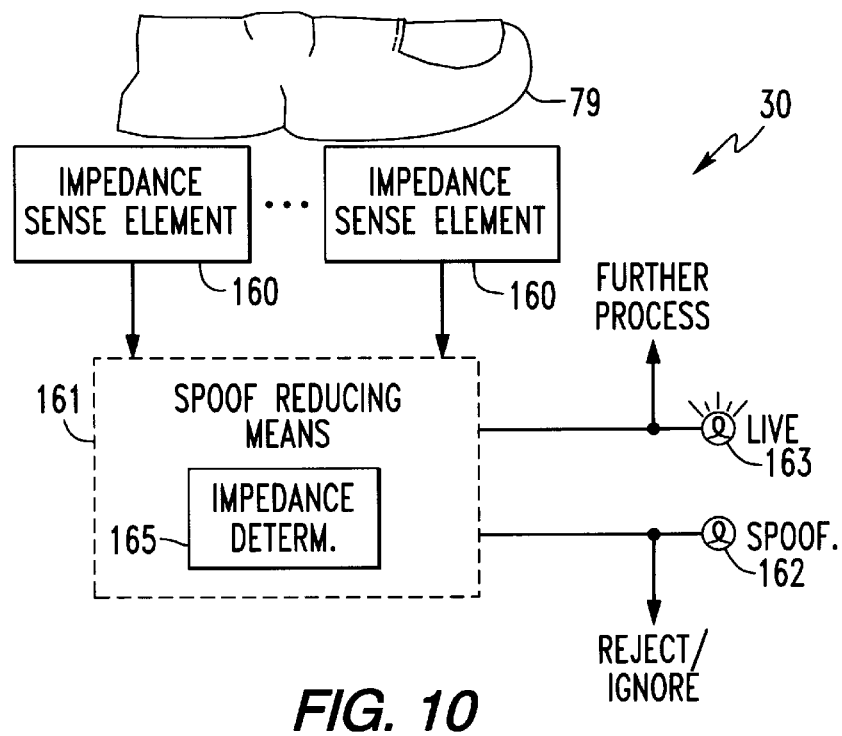
FIG. 10 is a schematic block diagram of still another circuit portion of the fingerprint sensor as shown in FIG. 1.

As shown in FIG. 10, the fingerprint sensor 30 may be considered as including an array of impedance sensing elements 160 for generating signals related to a finger 79 or other object positioned adjacent thereto. In the embodiment described herein, the impedance sensing elements 160 are provided by electric field sensing electrodes 78 and amplifiers 73 (FIG. 2) associated therewith. In addition, a guard shield 80 may be associated with each electric field sensing electrode 78 and connected to a respective amplifier 73. Spoof reducing means 161 is provided for determining whether or not an impedance of the object positioned adjacent the array of impedance sensing elements 160 corresponds to a live finger 79 to thereby reduce spoofing of the fingerprint sensor by an object other an a live finger. A spoofing may be indicated, such as by the schematically illustrated lamp 163 and/or used to block further processing. Alternately, a live fingerprint determination may also be indicated by a lamp 164 and/or used to permit further processing of the fingerprint image as will be readily appreciated by those skilled in the art. Many other options for indicating a live fingerprint or an attempted spoofing will be readily appreciated by those skilled in the art.

In one embodiment, the spoof reducing means 161 may include impedance determining means 165 to detect a complex impedance having a phase angle in a range of about 10 to 60 degrees corresponding to a live finger 79. Alternately, the spoof reducing means 161 may detect an impedance having a phase angle of about 0 degrees corresponding to some objects other than a live finger, such as a sheet of paper having an image thereon, for example. In addition, the spoof reducing means 161 may detect an impedance of 90 degrees corresponding to other objects.

Figure 11:
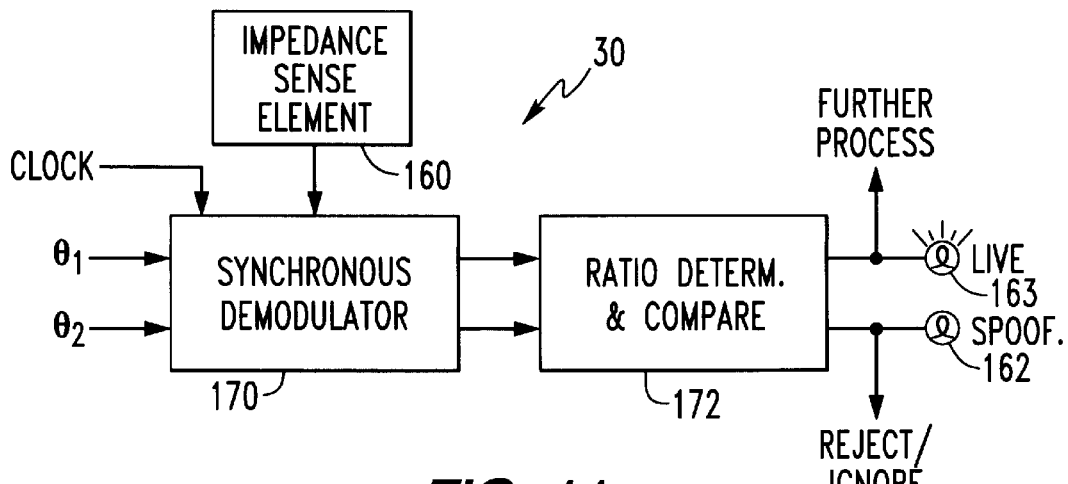
FIG. 11 is a schematic block diagram of an alternate embodiment of the circuit portion shown in FIG. 10.

Turning now to FIG. 11, another embodiment of spoof reducing means is explained. The fingerprint sensor 30 may preferably includes drive means for driving the array of impedance sensing elements 160, such as the illustrated excitation amplifier 74 (FIG. 2). The sensor also includes synchronous demodulator means 170 for synchronously demodulating signals from the array of impedance sensing elements 160. Accordingly, in one particularly advantageous embodiment of the invention, the spoof reducing means comprises means for operating the synchronous demodulator means 170 at at least one predetermined phase rotation angle. For example, the synchronous demodulator means 170 could be operated in a range of about 10 to 60 degrees, and the magnitude compared to a predetermined threshold indicative of a live fingerprint. A live fingerprint typically has a complex impedance within the range of 10 to 60 degrees.

Alternately, ratio generating and comparing means 172 may be provided for cooperating with the synchronous demodulator means 170 for synchronously demodulating signals at first and second phase angles $\theta_1$, $\theta_2$, generating an amplitude ratio thereof, and comparing the amplitude ratio to a predetermined threshold to determine whether the object is a live fingerprint or other object. Accordingly, the synchronous demodulator 170 may be readily used to generate the impedance information desired for reducing spoofing of the sensor 30 by an object other than a live finger. The first angle $\theta_1$ and the second $\theta_2$ may have a difference in a range of about 45 to 90 degrees, for example. Other angles are also contemplated by the invention as would be readily appreciated by those skilled in the art.

The fingerprint sensor 30 also includes an automatic gain control feature to account for a difference in intensity of the image signals generated by different fingers or under different conditions, and also to account for differences in sensor caused by process variations. It is important for accurately producing a fingerprint image, that the sensor can discriminate between the ridges and valleys of the fingerprint. Accordingly, the sensor 30 includes a gain control feature, a first embodiment of which is understood with reference to FIG. 12.

Figure 12:
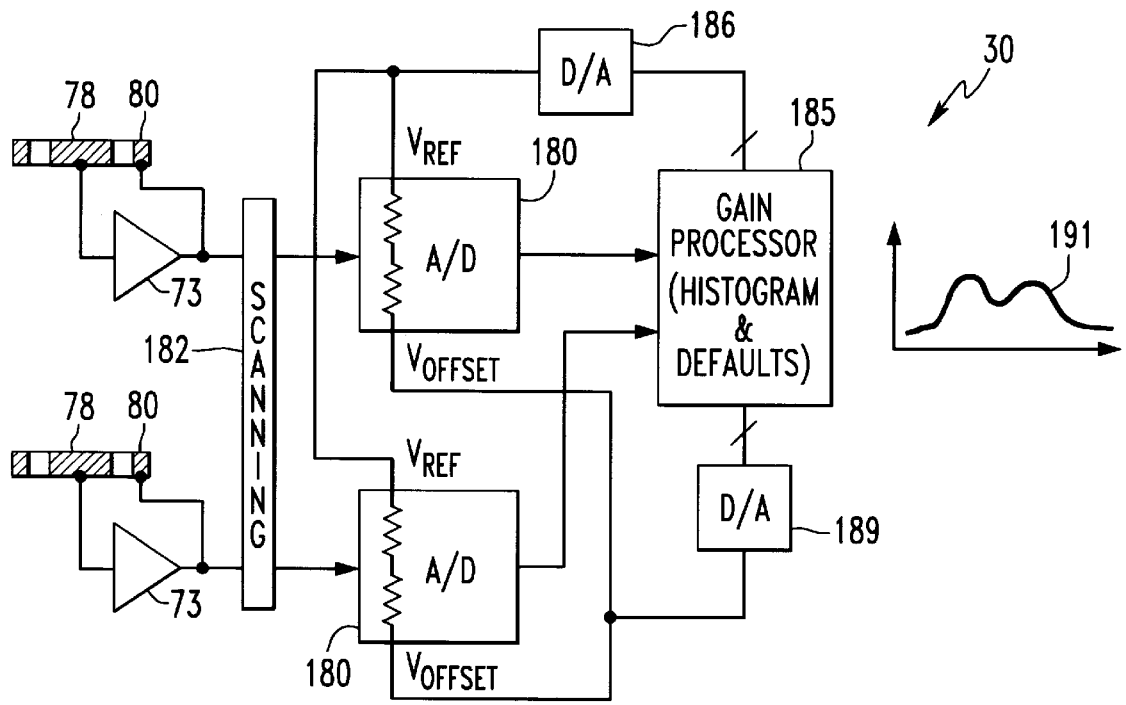
FIG. 12 is a schematic block diagram of an additional circuit portion of the fingerprint sensor as shown in FIG. 1

As shown in FIG. 12, the illustrated portion of the fingerprint sensor 30 includes an array of fingerprint sensing elements in the form of the electric field sensing electrodes 78 and surrounding shield electrodes 80 connected to the amplifiers 73. Other fingerprint sensing elements may also benefit from the following automatic gain control implementations as will be appreciated by those skilled in the art.

The signal processing circuitry of the sensor 30 preferably includes a plurality of analog-to-digital (A/D) converters 180 as illustrated. Moreover, each of these A/D converters 180 may have a controllable scale. Scanning means 182 sequentially connects different elements to the bank of A/D converters 180. The illustrated gain processor 185 provides range determining and setting means for controlling the range of the A/D converters 180 based upon prior A/D conversions to thereby provide enhanced conversion resolution. The A/D converters 180 may comprise the illustrated reference voltage input $V_{ref}$ and offset voltage input $V_{offset}$ for permitting setting of the range as would be readily appreciated by those skilled in the at. Accordingly, the range determining and setting means may also comprise a first digital-to-analog D/A converter 186 connected between the gain processor 185 and the reference voltage $V_{ref}$ inputs of the A/D converters 180 as would also be readily understood by those skilled in the art. In addition, a second D/A converter 189 is also illustratively connected to the offset voltage inputs $V_{offset}$ from the gain processor 185.

The gain processor 185 may comprise histogram generating means for generating a histogram, as described above, and based upon prior A/D conversions. The graph adjacent the gain processor 185 in FIG. 12 illustrates a typical histogram plot 191. The histogram plot 191 includes two peaks corresponding to the sensed ridges and valleys of the fingerprint as would be readily appreciated by those skilled in the art. By setting the range for the A/D converters 180, the peaks can be readily positioned as desired to thereby account for the variations discussed above and use the full resolution of the A/D converters 180.

Figure 13:
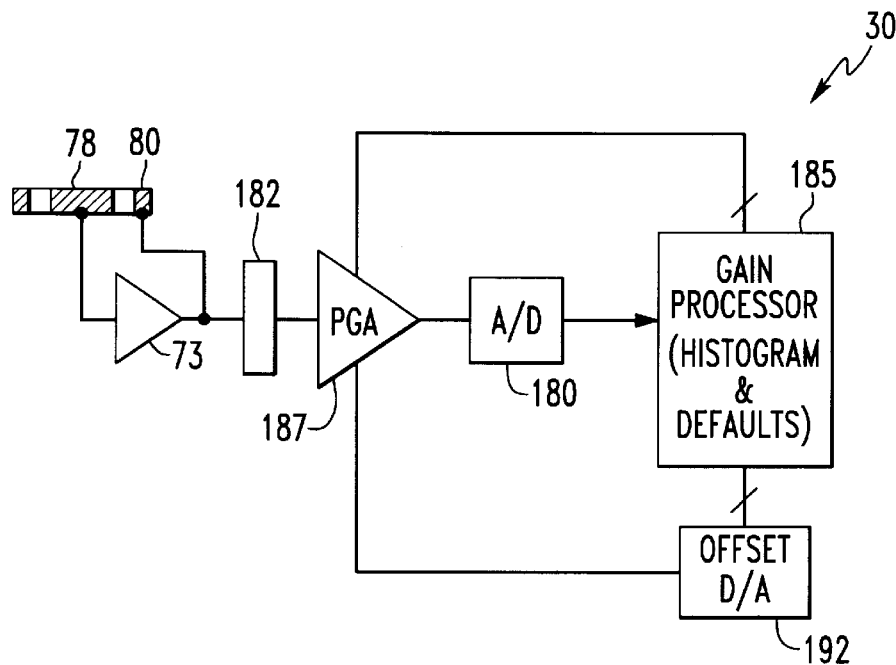
FIG. 13 is a schematic block diagram of an alternate embodiment of the circuit portion shown in FIG. 12.

Turning additionally to FIG. 13, the A/D converters 180 may include an associated input amplifier for permitting setting of the range. In this variation, the range determining and setting means may also comprise the illustrate gain processor 185, and wherein the amplifier is a programmable gain amplifier (PGA) 187 connected to the processor. A digital word output from the gain processor 185 sets the gain of the PGA 187 so that full use of the resolution of the A/D converters 180 is obtained for best accuracy. A second digital word output from the gain processor 185 and coupled to the amplifier 187 through the illustrated D/A converter 192 may also control the offset of the amplifier as would also be readily appreciated by those skilled in the art.

The range determining and setting means of the gain processor 185 may comprise default setting means for setting a default range for initial ones of the fingerprint sensing elements. The automatic gain control feature of the present invention allows the D/A converters 180 to operate over their full resolution range to thereby increase the accuracy of the image signal processing.

Other aspects, advantages, and features relating to sensing of fingerprints are disclosed in copending U.S. patent application Ser. No. 08/592,469 entitled "Electric Field Fingerprint Sensor and Related Methods", and U.S. patent application Ser. No. 08/671,430 entitled "Integrated Circuit Device Having an Opening Exposing the Integrated Circuit Die and Related Methods", both assigned to the assignee of the present invention, and the entire disclosures of which are incorporated herein by reference. In addition, many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A fingerprint sensor comprising:
   an integrated circuit die comprising at least one conductive layer defining an array of electric field sensing electrodes for sensing a fingerprint; and
   a dielectric covering adjacent the array of electric field sensing electrodes of said integrated circuit die and for contact by a finger, said dielectric covering comprising a z-axis anisotropic dielectric layer for focussing an electric field at each of the electric field sensing electrodes, the z-axis being normal to the at least one conductive layer.

2. A fingerprint sensor according to claim 1 wherein said z-axis anisotropic dielectric layer defines an outermost protective surface for said integrated circuit die.

3. A fingerprint sensor according to claim 1 wherein said z-axis anisotropic dielectric layer has a thickness in range of about 0.0001 to 0.004 inches.

4. A fingerprint sensor according to claim 1 wherein said z-axis anisotropic dielectric layer is chemically resistant and mechanically strong.

5. A fingerprint sensor according to claim 1 wherein said z-axis anisotropic dielectric layer comprises a plurality of oriented dielectric particles in a cured matrix.

6. A fingerprint sensor according to claim 1 wherein said z-axis anisotropic dielectric layer comprises barium titanate in a polyimide matrix.

7. A fingerprint sensor according to claim 1 wherein said z-axis anisotropic layer comprises an array of high dielectric portions aligned with corresponding electric field sensing electrodes, and a matrix of low dielectric portions surrounding the high dielectric portions.

8. A fingerprint sensor according to claim 1 wherein said dielectric covering further comprises at least one relatively thin layer of an oxide, nitride, carbide, and diamond on said integrated circuit die and beneath said z-axis anisotropic dielectric layer.

9. A fingerprint sensor according to claim 1 wherein said at least one conductive layer comprises a plurality of capacitive coupling pads for permitting capacitive coupling with said integrated circuit die; and wherein said dielectric covering is continuous over said capacitive coupling pads and the array of electric field sensing electrodes whereby the z-axis dielectric layer reduces cross-talk between adjacent capacitive coupling pads.

10. A fingerprint sensor according to claim 1 further comprising a package surrounding said integrated circuit die and dielectric covering, and wherein said package has an opening aligned with the array of electric field sensing electrodes.

11. A fingerprint sensor according to claim 10 further comprising at least one finger contacting electrode carried by said package and electrically connected to said integrated circuit die.

12. A sensor comprising:
   an integrated circuit die comprising at least one conductive layer defining an array of electric field sensing electrodes and a plurality of capacitive coupling pads; and
   a dielectric covering adjacent the array of electric field sensing electrodes and said capacitive coupling pads of said integrated circuit die, said dielectric covering comprising a z-axis anisotropic dielectric layer for focussing an electric field at each of the electric field sensing electrodes and for reducing cross-talk between adjacent capacitive coupling pads, the z-axis being normal to the at least one conductive layer.

13. A sensor according to claim 12 wherein said z-axis anisotropic dielectric layer defines an outermost protective surface for said integrated circuit die.

14. A sensor according to claim 12 wherein said z-axis anisotropic dielectric layer has a thickness in range of about 0.0001 to 0.004 inches.

15. A sensor according to claim 12 wherein said z-axis anisotropic dielectric layer is chemically resistant and mechanically strong.

16. A sensor according to claim 12 wherein said z-axis anisotropic dielectric layer comprises a plurality of oriented dielectric particles in a cured matrix.

17. A sensor according to claim 12 wherein said z-axis anisotropic dielectric layer comprises barium titanate in a polyimide matrix.

18. A sensor according to claim 12 wherein said z-axis anisotropic layer comprises an array of high dielectric portions aligned with corresponding electric field sensing electrodes, and a matrix of low dielectric portions surrounding the high dielectric portions.

19. A sensor according to claim 12 wherein said dielectric covering further comprises at least one relatively thin layer of an oxide, nitride, carbide, and diamond on said integrated circuit die and beneath said z-axis anisotropic dielectric layer.

20. A sensor according to claim 12 further comprising a package surround said integrated circuit die and dielectric covering, and wherein said package has an opening aligned with the array of electric field sensing electrodes.

21. A sensor according to claim 12 further comprising at least one finger contacting electrode carried by said package and electrically connected to said integrated circuit die so that the sensor is a fingerprint sensor.

22. A integrated circuit comprising:
an integrated circuit die comprising at least one conductive layer defining a plurality of capacitive coupling pads; and
a dielectric covering adjacent said capacitive coupling pads of said integrated circuit die, said dielectric covering comprising a z-axis anisotropic dielectric layer for reducing cross-talk between adjacent capacitive coupling pads, the z-axis being normal to the at least one conductive layer.

23. An integrated circuit according to claim 22 wherein said z-axis anisotropic dielectric layer defines an outermost protective surface for said integrated circuit die.

24. An integrated circuit according to claim 22 wherein said z-axis anisotropic dielectric layer has a thickness in range of about 0.0001 to 0.004 inches.

25. A integrated circuit according to claim 22 wherein said z-axis anisotropic dielectric layer is chemically resistant and mechanically strong.

26. An integrated circuit according to claim 22 wherein said z-axis anisotropic dielectric layer comprises a plurality of oriented dielectric particles in a cured matrix.

27. An integrated circuit according to claim 22 wherein said z-axis anisotropic dielectric layer comprises barium titanate in a polyimide matrix.

28. A integrated circuit according to claim 22 wherein said z-axis anisotropic layer comprises an array of high dielectric portions aligned with corresponding electric field sensing electrodes, and a matrix of low dielectric portions surrounding the high dielectric portions.

29. An integrated circuit according to claim 22 wherein said dielectric covering further comprises at least one relatively thin layer of an oxide, nitride, carbide, and diamond on said integrated circuit die and beneath said z-axis anisotropic dielectric layer.

30. An integrated circuit according to claim 22 further comprising a package surrounding said integrated circuit die and dielectric covering.

31. A integrated circuit comprising:
an integrated circuit die; and
a dielectric covering adjacent said integrated circuit die, said dielectric covering comprising a z-axis anisotropic dielectric layer, the z-axis being normal to the integrated circuit die.

32. An integrated circuit according to claim 31 wherein said z-axis anisotropic dielectric layer defines an outermost protective surface for said integrated circuit die.

33. An integrated circuit according to claim 31 wherein said z-axis anisotropic dielectric layer has a thickness in range of about 0.0001 to 0.004 inches.

34. An integrated circuit according to claim 31 wherein said z-axis anisotropic dielectric layer is chemically resistant and mechanically strong.

35. An integrated circuit according to claim 31 wherein said z-axis anisotropic dielectric layer comprises a plurality of oriented dielectric particles in a cured matrix.

36. An integrated circuit according to claim 31 wherein said z-axis anisotropic dielectric layer comprises barium titanate in a polyimide matrix.

37. An integrated circuit according to claim 31 wherein said z-axis anisotropic layer comprises an array of high dielectric portions aligned with corresponding electric field sensing electrodes, and a matrix of low dielectric portions surrounding the high dielectric portions.

38. An integrated circuit according to claim 31 wherein said dielectric covering further comprises at least one relatively thin layer of an oxide, nitride, carbide, and diamond on said integrated circuit die and beneath said z-axis anisotropic dielectric layer.

39. An integrated circuit according to claim 31 further comprising a package surrounding said integrated circuit die and dielectric covering.

40. A method for making a fingerprint sensor comprising the steps of:
forming an integrated circuit die comprising at least one conductive layer defining an array of electric field sensing electrodes for sensing a fingerprint; and
forming a dielectric covering adjacent the array of electric field sensing electrodes of the integrated circuit die and for contact by a finger, the dielectric covering comprising a z-axis anisotropic dielectric layer for focussing an electric field at each of the electric field sensing electrodes, the z-axis being normal to the at least one conductive layer.

41. A method according to claim 40 wherein the step of forming the dielectric covering comprises forming same so that the z-axis anisotropic dielectric layer defines an outermost protective surface for the integrated circuit die.

42. A method according to claim 40 wherein the step of forming the dielectric covering comprises forming same so that the z-axis anisotropic dielectric layer has a thickness in range of about 0.0001 to 0.004 inches.

43. A method according to claim 40 wherein the step of forming the dielectric covering comprises forming same so that the z-axis anisotropic dielectric layer is chemically resistant and mechanically strong.

44. A method according to claim 40 wherein the step of forming the dielectric covering comprises forming same so that the z-axis anisotropic dielectric layer comprises a plurality of oriented dielectric particles in a cured matrix.

45. A method according to claim 40 wherein the step of forming the dielectric covering comprises forming same so that the z-axis anisotropic dielectric layer comprises barium titanate in a polyimide matrix.

46. A method according to claim 40 wherein the step of forming the dielectric covering comprises forming same so that the z-axis anisotropic layer comprises an array of high dielectric portions aligned with corresponding electric field sensing electrodes, and a matrix of low dielectric portions surrounding the high dielectric portions.

47. A method according to claim 40 wherein the dielectric covering further comprises at least one relatively thin layer of an oxide, nitride, carbide, and diamond on the integrated circuit die and beneath the z-axis anisotropic dielectric layer.

48. A method according to claim 40 wherein the step of forming the at least one conductive layer further comprises forming same to include a plurality of capacitive coupling pads for permitting capacitive coupling with the integrated circuit die; and wherein the step of forming the dielectric covering comprises forming same to be continuous over the capacitive coupling pads and the array of electric field sensing electrodes whereby the z-axis dielectric layer reduces cross-talk between adjacent capacitive coupling pads.

49. A method according to claim 40 further comprising the step of forming a package surrounding the integrated circuit die and dielectric covering, and wherein the package has an opening aligned with the array of electric field sensing electrodes.

50. A method of making an integrated circuit comprising:

providing an integrated circuit die; and forming a dielectric covering adjacent the integrated circuit die, the dielectric covering comprising a z-axis anisotropic dielectric layer, the z-axis being normal to the integrated circuit die.

51. A method according to claim 50 wherein the step of forming the dielectric covering comprises forming same so that the z-axis anisotropic dielectric layer defines an outermost protective surface for the integrated circuit die.

52. A method according to claim 50 wherein the step of forming the dielectric covering comprises forming same so that the z-axis anisotropic dielectric layer has a thickness in range of about 0.0001 to 0.004 inches.

53. A method according to claim 50 wherein the step of forming the dielectric covering comprises forming same so that the z-axis anisotropic dielectric layer is chemically resistant and mechanically strong.

54. A method according to claim 50 wherein the step of forming the dielectric covering comprises forming same so that the z-axis anisotropic dielectric layer comprises a plurality of oriented dielectric particles in a cured matrix.

55. A method according to claim 50 wherein the step of forming the dielectric covering comprises forming same so that the z-axis anisotropic dielectric layer comprises barium titanate in a polyimide matrix.

56. A method according to claim 50 wherein the step of forming the dielectric covering comprises forming same so that the z-axis anisotropic layer comprises an array of high dielectric portions aligned with corresponding electric field sensing electrodes, and a matrix of low dielectric portions surrounding the high dielectric portions.

57. A method according to claim 50 wherein the dielectric covering further comprises at least one relatively thin layer of an oxide, nitride, carbide, and diamond on the integrated circuit die and beneath the z-axis anisotropic dielectric layer.

58. A method according to claim 50 further comprising the step of forming a package surrounding the integrated circuit die and dielectric covering.

* * * * *